US008314613B2

(12) United States Patent
Cui et al.

(10) Patent No.: US 8,314,613 B2
(45) Date of Patent: Nov. 20, 2012

(54) ELECTROCHEMICAL BIOSENSOR MEASURING SYSTEM

(75) Inventors: Gang Cui, Seoul (KR); Keun Ki Kim, Seoul (KR); Dong Hoon Han, Seoul (KR); Moon Hwan Kim, Seoul (KR); Hakhyun Nam, Seoul (KR); Geun Sig Cha, Seoul (KR)

(73) Assignee: i-SENS, Inc., Seoul (KR)

( * ) Notice: Subject to any disclaimer, the term of this patent is extended or adjusted under 35 U.S.C. 154(b) by 425 days.

(21) Appl. No.: 12/672,596

(22) PCT Filed: Feb. 26, 2008

(86) PCT No.: PCT/KR2008/001106
§ 371 (c)(1),
(2), (4) Date: Feb. 8, 2010

(87) PCT Pub. No.: WO2009/022779
PCT Pub. Date: Feb. 19, 2009

(65) Prior Publication Data
US 2011/0210726 A1    Sep. 1, 2011

(30) Foreign Application Priority Data
Aug. 10, 2007   (KR) .................. 10-2007-0080588

(51) Int. Cl.
*G01V 3/00*   (2006.01)

(52) U.S. Cl. .......... 324/252; 324/244; 204/403.01; 204/403.02; 204/403.1; 205/777.5; 205/792; 600/347

(58) Field of Classification Search ....... 204/403.01–403.15, 403.1; 205/777.5, 205/792; 600/347
See application file for complete search history.

(56) References Cited

U.S. PATENT DOCUMENTS
4,714,874 A   12/1987 Morris et al.
(Continued)

FOREIGN PATENT DOCUMENTS
| JP | 2-216057 | 8/1990 |
| JP | 10-340405 | 12/1998 |
| JP | 11-265421 | 9/1999 |
| JP | 11-304748 | 11/1999 |
| JP | 2000-275255 | 10/2000 |

(Continued)

OTHER PUBLICATIONS

International Search Report for Application No. PCT/KR2008/001108, dated May 29, 2008.

*Primary Examiner* — Jermele M Hollington
*Assistant Examiner* — Alesa Allgood
(74) *Attorney, Agent, or Firm* — Nelson Mullins Riley & Scarborugh LLP; EuiHoon Lee, Esq.

(57) ABSTRACT

Disclosed are an electrochemical biosensor which comprises a production lot information identification portion, on which information is recorded in a magnetization mark, and a measuring device which can automatically identify the production lot information of the biosensor with the insertion of the electrochemical biosensor into the measuring device. The electrochemical biosensor and the measuring device thereof can record production lot information in the form of magnetization marks on an electrochemical biosensor strip and read the information as digital signals through a magnetoresistance sensor device, which can be mounted on the surface of a circuit board using Surface Mounted Technology (SMT). Without the need for a high-priced filter or a complicated calculation system, the magnetic detector system has a simple construction and realizes economic efficiency in the construction of the measuring device. Also, the measuring device automatically identifies the production lot information recorded on the biosensor, so that inconvenience and the frequency of errors, which occur when a user personally inputs the production lot information, can be reduced, with the result that the measured values can be conveniently and accurately acquired.

7 Claims, 2 Drawing Sheets

U.S. PATENT DOCUMENTS

| | | | |
|---|---|---|---|
| 6,814,844 B2 * | 11/2004 | Bhullar et al. | 204/403.01 |
| 7,015,046 B2 * | 3/2006 | Wohlstadter et al. | 436/172 |
| 7,190,049 B2 * | 3/2007 | Tuominen et al. | 257/618 |
| 2005/0089449 A1 * | 4/2005 | Polwart et al. | 422/100 |
| 2008/0032490 A1 * | 2/2008 | Tuominen et al. | 438/466 |

FOREIGN PATENT DOCUMENTS

| | | |
|---|---|---|
| JP | 2001-147230 | 5/2001 |
| KR | 10-2006-0089464 | 8/2006 |
| WO | 2007/050396 A1 | 5/2007 |

* cited by examiner

ELECTROCHEMICAL BIOSENSOR MEASURING SYSTEM

RELATED APPLICATIONS

This application is a 35 U.S.C. §371 national stage filing of PCT Application No. PCT/KR2008/001106 filed on Feb. 26, 2008, which claims priority to, and the benefit of, Korean Patent Application No. 10-2007-0080588 filed on Aug. 10, 2007. The contents of the aforementioned applications are hereby incorporated by reference.

TECHNICAL FIELD

The present invention relates to an electrochemical biosensor and a biosensor measuring device.

BACKGROUND ART

For the diagnosis and prophylaxis of diabetes mellitus, the importance of periodic monitoring of blood glucose levels has been increasingly emphasized. Nowadays, strip-type biosensors designed for hand-held reading devices allow individuals to readily monitor glucose levels in the blood.

A large number of commercialized biosensors measure blood glucose present in blood samples using an electrochemical technique. The principle of the electrochemical technique is based on the following Reaction 1.

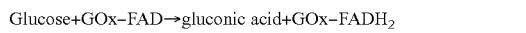

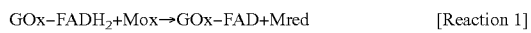 [Reaction 1]

wherein GOx represents glucose oxidase; GOx–FAD and GOx–FADH$_2$ respectively represent an oxidized and a reduced state of glucose-associated FAD (flavin adenine dinucleotide), a cofactor required for the catalyst of glucose oxidase; and Mox and Mred denote an oxidized and a reduced state, respectively, of an electron transfer mediator.

The electrochemical biosensor uses as electron transfer mediators organic electron transfer materials, such as ferrocenes or their derivatives, quinines or their derivatives, organic or inorganic materials containing transition metals (hexamine ruthenium, polymer containing osmium, potassium ferricyanide and the like), organic conducting salts, and viologens.

The principle by which blood glucose is measured using the biosensor is as follows.

Glucose in the blood is oxidized to gluconic acid by the catalysis of glucose oxidase, with the cofactor FAD reduced to FADH2. Then, the reduced cofactor FADH$_2$ transfers electrons to the mediator, so that FADH$_2$ returns to its oxidized state; that is, FAD and the mediator are reduced. The reduced mediator is diffused to the surface of the electrodes. The series of reaction cycles is driven by the anodic potential applied at the working electrode, and the redox current proportional to the level of glucose is measured. Over biosensors based on colorimetry, the electrochemical biosensors (that is, based on electrochemistry) have the advantages of not being influenced by the turbidity or color of the samples and allowing the use of wider range of samples, even cloudy ones, without pretreatment thereof.

Although this electrochemical biosensor is generally conveniently used to monitor and control the amount of blood glucose, its accuracy is greatly dependent on deviations according to each mass-production lot in which the biosensors are produced. In order to eliminate this deviation, most commercialized biosensors are designed such that a user directly inputs calibration curve information, which is predetermined at the factory, into a measuring device capable of reading the biosensor. However, this method is highly inconvenient for the user and causes the user to make input errors, thus leading to inaccurate results.

In order to solve such problems, a method by which the resistance of each electrode can be adjusted such that the variations in mass production is corrected (US20060144704A1), a method in which a conductor is printed in a bar code fashion on the biosensor strip to record the production information (U.S. Pat. No. 6,814,844), a method in which a connection to a resistor bank is made (WO2007011569A2), and a method by which information is read by varying resistance through the adjustment of the length or thickness of each electrode (US20050279647A1) have been proposed. The methods proposed for the electrochemical biosensors are all based on a technique with which electrical variation can be read. Furthermore, a method for distinguishing production lot information by reading the resistivity of a conductor marked on a strip using an electrical method (U.S. Pat. No. 4,714,874) has been proposed.

However, these methods serve to accurately adjust resistance, and require a process of mass-producing the sensors first, measuring the statistical characteristics of the sensors, and post-processing the measured information again using a method of adjusting the resistance marked on the sensors. However, the process of accurately adjusting the resistance, marked in large quantities, through the post-processing is very inconvenient, and is difficult to use for practical application.

Methods in which colored marks are used to enable a spectral system capable of discriminating colors to use a colorimetric method (U.S. Pat. Nos. 3,907,503, 5,597,532, 6,168,957), a method in which a plurality of color marks is read at various wavelengths of visible and infrared ray regions using a spectroscope (U.S. Pat. No. 5,945,341), and a method in which bar codes are read (EP00075223B1, WO02088739A1) have been proposed. These methods, using color or bar codes, are favorable for a colorimetric method-based sensor using the spectrum system, but they have technical and economic difficulties when applied to systems using an electrochemical measurement mechanism. For example, the size and structure of the portion where the electrochemical sensor strip is inserted into the measuring device for the purpose of electrical connection, that is, the connection space of the sensor strip, is very limited when constructing a device and circuit for spectroscopically identifying the structure into which the production lot information is input. Further, color discrimination requires a process of scattering and identifying various wavelengths of light detected using a detector and a complicated process, that is, the conversion of analog signals into digital signals and the calculation thereof, with the concomitant accompaniment of a device and its program therefor. Thus, the expenses incurred when constructing the system are greatly increased.

Furthermore, instead of the methods of marking the production lot information on the sensor strip, a method of recording information on a container or pack containing a sensor and allowing the information to be read by the measuring device (EP0880407B1) has been proposed. However, this method also has a possibility of causing the user to make an error of incorrectly reading a code recorded on the container.

Leading to the present invention, intensive and thorough research into electrochemical biosensors, conducted by the present inventors, aiming to maintain economic efficiency in the construction of the measuring device while allowing the mass production of the electrochemical biosensor, which allows the production lot information thereof to be easily and accurately input into the measuring device without mistakes on the part of the user, and thus provides an accurate measurement value, resulted in the finding that, when the production lot information is recorded in the form of magnetization marks on the electrochemical biosensor strip and read in the measuring device, a micro magnetoresistance sensor device can be employed to detect the magnetization marks, without the need for a high-priced magnetic reader, so that the magnetic detector system has a simple construction and thus can not only reduce a complicated calculation process, performed for post-treatment, but also maintain economic efficiency in the construction of the measuring device.

DISCLOSURE OF INVENTION

Technical Problem

Accordingly, the present invention has been made keeping in mind the above problems occurring in the prior art, and an object of the present invention is to provide an electrochemical biosensor comprising a magnetization mark and a measuring device thereof, which can automatically identify the production lot information of the biosensor with the insertion of the electrochemical biosensor into the measuring device, evaluates blood glucose levels accurately and conveniently, and is economically favorable.

Technical Solution

In order to accomplish the above object, the present invention provides an electrochemical biosensor, composed of plurality of electrodes including at least a working electrode and an auxiliary electrode prepared on at least one or two insulating plates; a capillary sample cell for introducing a sample into the electrodes; a reaction reagent layer, formed on the working electrode, containing a redox enzyme and an electron transfer mediator; an electrical connection portion for connecting the working electrode and the auxiliary electrode; and a production lot information identification portion configured such that production lot information is recorded on at least one insulating plate, which is selected from among at least two planar insulating plates and does not interrupt a connection between the electrodes, wherein the production lot information identification portion, on which the production lot information is recorded, includes a magnetization mark, formed by printing magnetic materials having different magnetic fields in a predetermined pattern or attaching magnetic films having different magnetic fields, for distinguishing information about production lot differences using this difference in magnetic field.

In addition, the present invention provides an electrochemical biosensor measuring device for quantitatively determining analytes using the electrochemical biosensor, comprising a magnetoresistance sensor device capable of detecting magnetic fields to identify the production lot information recorded on the production lot information identification portion of the biosensor.

ADVANTAGEOUS EFFECTS

The electrochemical biosensor comprises a production lot information identification portion on which information is recorded in a magnetization mark, and the measuring device can automatically identify the production lot information of the biosensor upon the insertion of the electrochemical biosensor into the measuring device. The electrochemical biosensor and the measuring device thereof in accordance with the present invention can record production lot information in the form of magnetization marks on an electrochemical biosensor strip and read the information as digital signals through a magnetoresistance sensor device, which can be mounted on the surface of a circuit board using Surface Mounted Technology (SMT). Without the need for a high-priced filter or a complicated calculation system, the magnetic detector system has a simple construction and ensures economic efficiency in the construction of the measuring device. Also, the measuring device automatically identifies the production lot information recorded on the biosensor, so that the frequency of inconvenience and error, which occur when a user personally inputs the production lot information, can be reduced, with the result that the measured values can be conveniently and accurately acquired.

BRIEF DESCRIPTION OF THE DRAWINGS

The above and other objects, features and advantages of the present invention will be more clearly understood from the following detailed description taken in conjunction with the accompanying drawings, in which.

BRIEF DESCRIPTION OF THE MARK OF DRAWINGS

Figure 1:
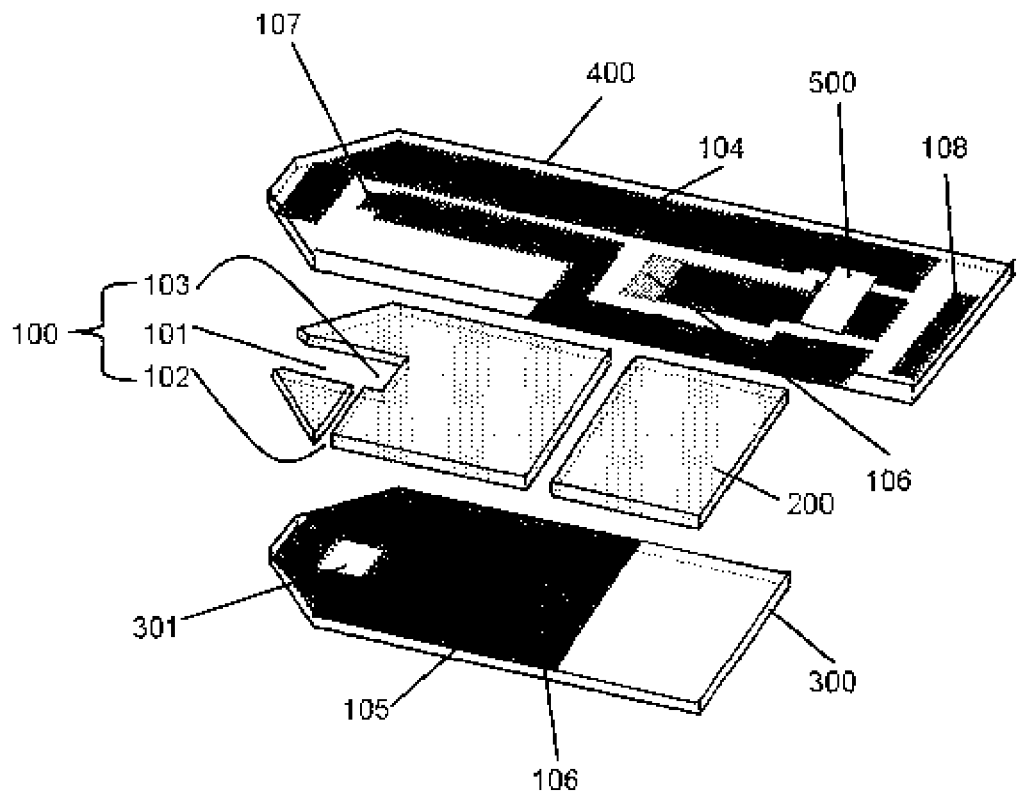
FIG. 1 is an exploded view of a biosensor, in which production lot information, indicated by magnetization marks, is recorded on the upper plate thereof, according to an embodiment of the present invention.

100: sample introduction portion
101: sample introducing pass
102: air vent
103: allowance space portion
104: working electrode
105: auxiliary electrode or reference electrode
106: electrode connection portion
107: sample fluidity determining electrode
108: biosensor confirming electrode
200: middle plate
300: upper plate
400: lower plate
500: production lot information identification portion
700: sensor connector
704: printed circuit board
705: electrical connection portion
800: magnetoresistance sensor device
→: magnetic field flow

BEST MODE FOR CARRYING OUT THE INVENTION

In the present specification, the term "biosensor" is used as having the same meaning as the term "biosensor strip".

In accordance with an aspect thereof, the present invention provides an electrochemical biosensor, composed of an electrodes including a working electrode and an auxiliary electrode prepared on at least two insulating plates; a capillary sample cell for introducing a sample into the electrodes; a reaction reagent layer, formed on the working electrode, containing an oxidation enzyme and an electron transfer mediator; an electrical connection portion for connecting the working electrode and the auxiliary electrode; and a production lot information identification portion, configured such that production lot information is recorded on at least one insulating plate, which is selected from among at least two planar insulating plates and does not interrupt connection between the electrodes, wherein the production lot information identification portion, on which the production lot information is recorded, includes a magnetization mark, formed by printing or attaching magnetic materials having different magnetic fields in a predetermined pattern, for distinguishing information about production lot differences using the difference in the magnetic fields.

The electrodes of the electrochemical biosensor used in the electrochemical biosensor measuring device according to the present invention may be formed on one or more of at least two planar insulating plates. That is, (1) a single working electrode and a single auxiliary electrode (or reference electrode) may be formed on the same planar insulating plate, or (2) may be formed on two planar insulating plates facing each other [parallel electrodes; reference: E. K. Bauman et al., Analytical Chemistry, vol 37, p 1378, 1965; K. B. Oldham in "Microelectrodes: Theory and Applications," Kluwer Academic Publishers, 1991; J. F. Cassidy et al., Analyst, vol 118, p 415].

In addition, the electrodes of the electrochemical biosensor used in the electrochemical biosensor measuring device according to the present invention may further include a sample fluidity determining electrode, which is disposed behind the working electrode and is capable of measuring the fluidity of complete blood samples on a lower planar insulating plate.

The biosensor is described in greater detail taking parallel electrodes as an example.

In the case where the electrochemical biosensor used for the electrochemical biosensor measuring device according to the present invention is constructed using the parallel electrodes, the biosensor may have a structure in which the working electrode and the auxiliary electrode are spaced apart from each other by a pressure-adhesive spacer 50-250 μm thick, and are aligned or not aligned with each other while facing each other.

In the thin spacer, a capillary sample cell on a microliter volume scale is provided for injecting a bio-sample in a measurement space defined by the working electrode and the auxiliary electrode and retaining the sample therein. The capillary sample cell includes a sample introducing portion and a micro-path.

In the thin spacer, a sample fluidity determining electrode is placed preferably at a predetermined distance from the working electrode or the auxiliary electrode so that fluorinated blood having a corpuscle volume of 40% can reach the working electrode (or the auxiliary electrode) along a micro-path 0.5-2 mm wide and 50-250 μm high within about 600 ms, and more preferably at a predetermined distance from the working electrode or the auxiliary electrode such that non-fluorinated blood can reach the electrode along the micro-path 0.5-2 mm wide and 50-250 μm high within 300 ms, and still more preferably within 200 ms.

Functioning to introduce a blood sample into one end of the biosensor, the sample-introducing portion is preferably formed in a "L" shape so as to allow the rapid, accurate and convenient introduction of a blood sample from the front end of the biosensor strip. The sample introducing portion is structured such that an allowance space is formed at the location at which a sample introducing path and an air vent cross each other. By the term "cross", as used herein, it is meant that the sample-introducing path and the air vent are not arranged parallel to each other, but intersect each other at a predetermined point. During measurement, the allowance space helps maintain a constant and accurate volume of the blood sample within the path while discharging the excess sample through the air vent. Also, the allowance space may be used as the place where the sample fluidity determining electrode is disposed. When introduced into the sample introducing portion, a blood sample moves to the electrodes through the micro-path.

In the electrochemical biosensor used in the electrochemical biosensor measuring device according to the present invention, the reaction reagent layer may be formed merely by applying a reagent solution only to the working electrode, or to both the working electrode and the sample fluidity determining electrode. The reaction reagent layer includes an enzyme, such as a glucose oxidase or a lactate oxidase, an electron transfer mediator, a water-soluble polymer, such as a cellulose acetate, a polyvinyl alcohol or a polypyrrol, a fatty acid having 4 to 20 carbon atoms as a reagent for reducing a hematocrit effect, and a hydrophilic quaternary ammonium salt.

In the electrochemical biosensor according to the present invention, electrode connection portions, at which the biosensor and the measuring device are electrically connected, are designed to exist in the same plane, in which the working electrode and auxiliary electrode are connected via connection lines. The level of blood glucose that is measured by the biosensor of the present invention from the results of an electrochemical reaction is provided to the measuring device through the electrode connection portions, and thus can be numerically converted into a precise blood glucose value.

The electrochemical biosensor according to the present invention includes a production lot information identification portion 500 for providing calibration curve information about various concentrations of liquid samples, which is used for respective production lots at the time of manufacturing the biosensor, along with biosensor production lot information, to a user.

The production lot information identification portion 500 may include magnetization marks displaying the information about differences between production lots by means of differences in magnetic field intensity, which are prepared by printing magnetic materials having different magnetic fields in a predetermined pattern or attaching a magnetic film. Particularly, when the magnetization marks are constructed by printing and magnetizing magnetic materials or attaching a magnetization film, information for the production lots of various kinds of biosensors can be marked without change in the figure design of the biosensor strip.

Preferably, the magnetic material or film has a magnetic field ranging in intensity from 0.01 to 15 Gauss.

Figure 2:
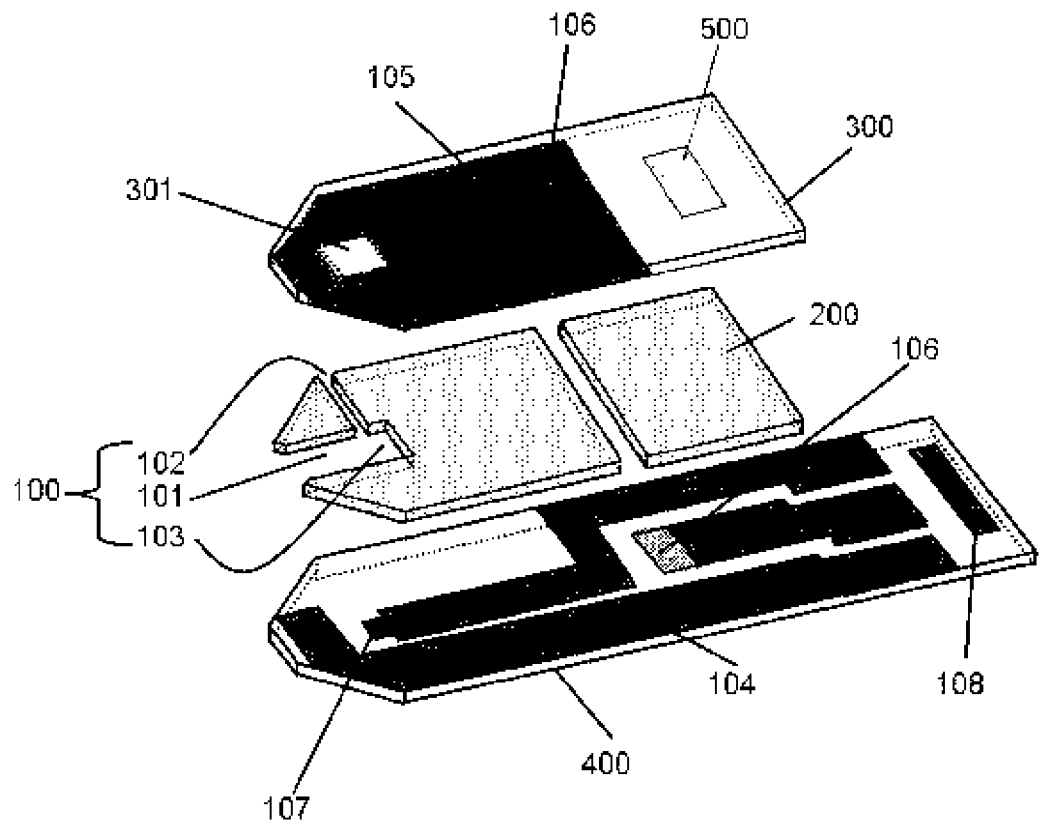
FIG. 2 is an exploded view of a biosensor, in which production lot information, indicated by magnetization marks, is recorded on the lower plate thereof, according to an embodiment of the present invention.

In the electrochemical biosensor according to the present invention, the number of magnetization marks is preferably adjusted to fall within the range of 1 to 10. The magnetization marks may be located on any of an upper plate (FIG. 1) or a lower plate (FIG. 2) as long as the connections of the electrodes 104, 105, 107 and 108 and the electrode connection portions 106 are not disturbed on the biosensor.

In accordance with another aspect thereof, the present invention provides an electrochemical biosensor measuring device for the quantitative analysis of analytes using the electrochemical biosensor, comprising a magnetoresistance sensor device capable of detecting the voltage difference attributable to the magnetic field of the magnetic material to identify the production lot information recorded on the production lot information identification portion of the biosensor.

In the electrochemical biosensor measuring device according to the present invention, a connector having a structure in which a production lot information identification portion-magnetic field detection path can be acquired may be used so as to identify the production lot information marked on the biosensor.

The connector, for example, may be formed of a body having transparent material, such as transparent acrylic and plastic.

Also, the connector may be provided with a transmission window in one side thereof so that a magnetic field can be formed through the production lot information identification portion-magnetic field detection portion. Accordingly, even when the connector is made of opaque material, or even when the body of the connector is colored, the light beams radiated by the light-emitting units can easily reach the production lot information identification portion of the biosensor through the transmission window, and thus the production lot information can be identified.

Furthermore, in order to form a magnetic field through the production lot information identification portion-magnetic field detection portion, the connector may be manufactured such that one side thereof has a sliding door structure. In greater detail, when a biosensor is inserted into the connector, the sliding door structure of the connector is pushed along with the biosensor in the insertion direction of the biosensor, thus realizing the path along which the light beams can reach the production lot information identification portion of the biosensor. In this case, the sliding door structure may be connected to a device that can passively or automatically remove the biosensor, and thus the biosensor can be easily separated and removed from the biosensor measuring device using the removing device after the use of the biosensor.

Figure 3:
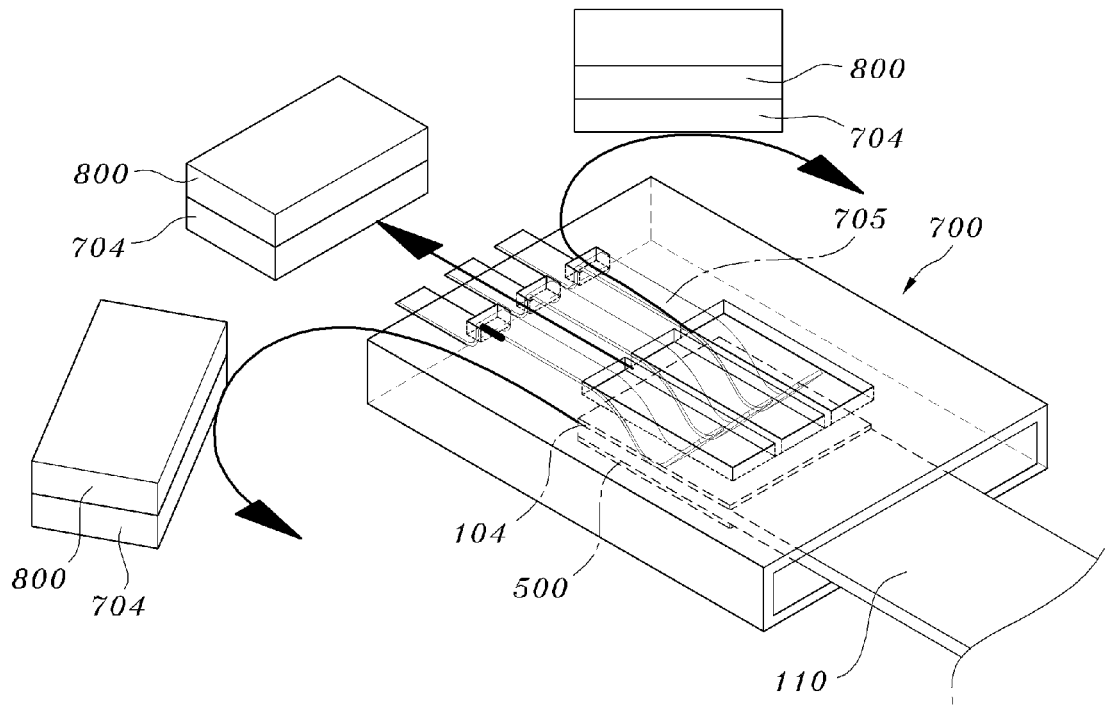
FIG. 3 is a schematic assembled view showing a combination of a biosensor with a biosensor measuring device comprising a magnetoresistance sensor device according to an embodiment of the present invention.
Figure 4:
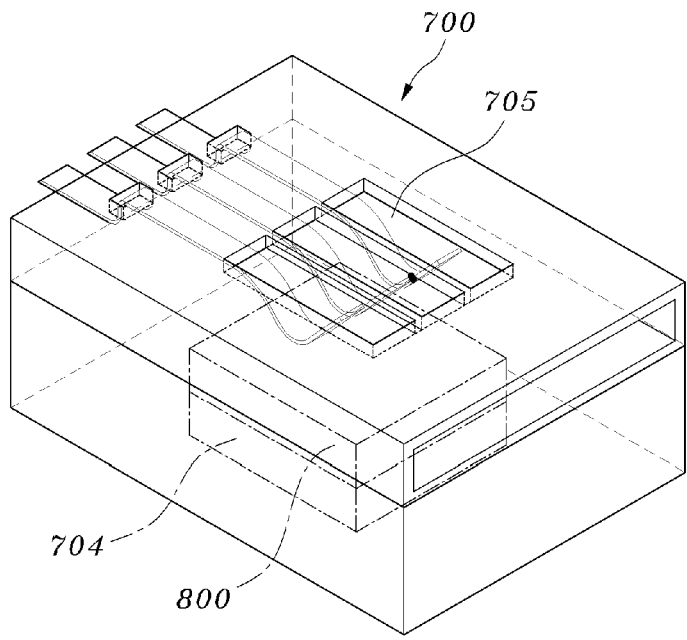
FIG. 4 is a perspective view of a biosensor measuring device comprising a sensor connector combined with a magnetoresistance sensor device in accordance with an embodiment of the present invention.

In the electrochemical biosensor measuring device according to the present invention, the magnetoresistance sensor device may be located inside or outside the connector of the measuring device. In greater detail, the magnetoresistance sensor device may be provided as a separate entity, as shown in FIG. 3, such that the detection path of the magnetic field can be acquired outside the connector, which allows the biosensor to be inserted thereinto, and can be connected therewith, or may be integrated into the connector, as shown in FIG. 4, such that the detection path of the magnetic field can be acquired in the upper or lower end portion of the connector.

It may be generally difficult or uneconomical to construct a system in which a magnetization mark identification circuit is installed in combination with a circuit and device for measuring the biosensor of an electrochemical system. With the recent development of anisotropic magnetoresistive technology (AMR), however, a system, the constitution of which was considered in the past as being unreasonable due to incompatibility between constitutional components, can be easily and economically implemented in a small circuit space at minimal cost.

Conventionally, for example, a magnetic identification sensor reads the information of magnetization marks as the magnetization marks move in contact with the magnetic identification sensor. The identification of the production lot information of the biosensor according to the present invention can be economically achieved by the magnetoresistance sensor device, which can read the magnetization marks into digital signals without contact. A commercialized magnetoresistance sensor device is very small, for example, it has a thickness of less than 2 mm and a size of 2×3 mm2, so that it can be mounted, along with typical electronic devices, on the surface of a circuit board using Surface Mounted Technology (SMT), and the construction thereof is very simple and economical. In particular, the magnetoresistance sensor device, which is installed inside or outside the connector for electrically connecting the biosensor using the SMT, is convenient to use, and can be constructed to be integrated with the biosensor for simplicity.

Furthermore, the magnetization marks can be identified according to the intensity of the magnetic field of the magnetic material, so that other variable details, for example, a calibrated curve for the production lots, the production time point of the biosensor, whether the product of the same manufacturer is used, and whether to sensor is to be used for a specific model of device, can be recorded. A combination of the advantages of such electrochemical measurement and the advantages of recent small-sized spectral device technologies obtained by the development of technology makes it possible to provide an economical and accurate biosensor.

The production lot information identification device using the magnetoresistance sensor device, which senses magnetic fields in the electrochemical biosensor measuring device according to the present invention, provides excellent performance and various advanced advantages when compared with devices that use conventional magnetic field identification methods. In contrast to a conventional magnetic identification sensor, the magnetoresistance sensor can detect magnetic fields without the contact or movement of a magnetic field identification portion, so that there is almost no concern of abnormal operation. Having these advantages, the magnetoresistance sensor consumes very little power. Accordingly, the production lot information identification device is highly appropriate for use with a small-sized biosensor device. Furthermore, with the ability to detect only the intensities of magnetic fields and to immediately output them into voltages to discriminate codes according to the voltages, the magnetoresistance sensor alone can constitute a circuit, thereby requiring neither separate amplification devices nor complicated circuits. Furthermore, the information read by the magnetoresistance sensor is electrical signals, so that a software process of converting analog signals into digital signals is not necessary, therefore the configuration of a program is extremely simplified. The biosensor measuring device using the above-described advantages of the magnetoresistance sensor causes almost no concern about abnormal operation, in contrast to other, conventional, color identification methods or a conventional method of identifying a bar code having a complicated pattern, and thus can provide highly reliable measurement results.

Also, the present invention provides a measuring method using a biosensor measuring device, comprising:

inserting a biosensor provided with a production lot identification portion containing production lot information into the connector port of the biosensor measuring device to activate its power (step 1);

identifying the production lot information of the inserted biosensor by allowing two or more magnetoresistance sensor devices to operate at the same time or in a sequential manner within the measuring device and to detect the information recorded on the production lot information identification portion provided in the biosensor (step 2);

activating measurement and operation processes of the biosensor measuring device in conformity with the production lot information identified at Step 2 (step 3); and introducing a liquid sample to the sample inlet of the biosensor to result in quantitative electrochemical information about the sample, quantifying a specific component of the liquid sample, and displaying quantification results (step 4).

The measuring method using the biosensor measuring device of the present invention is described stepwise in detail below.

In step 1, a biosensor provided with a production lot identification portion containing production lot information into the connector port of the biosensor measuring device is inserted to activate its power.

The biosensor is inserted into the measuring device through a sensor injection hole. Upon insertion, the electrodes of the biosensor are electrically connected to the electrical connection portions of the connector to allow electric current to flow, therefore operating the measuring device.

Next, Step 2 serves to identify the production lot information of the biosensor which is inserted at step 1. In this regard, magnetoresistance sensors are operated to read the intensity of the magnetic field recorded on the production lot information identification portion provided in the biosensor.

The insertion of the biosensor into the connector electrically connects the biosensor to the measuring device through the connector to activate the magnetoresistance sensor device in the measuring device, thereby identifying the production lot information of the biosensor from the activated magnetoresistance sensor device.

The production lot information identification portion may include one or more magnetization marks, which indicate information about differences between production lots through the printing of magnetic materials having differences in the intensity of magnetic field in conformity with a predetermined pattern. In this case, it is preferred that the number of magnetization marks be adjusted to fall within the range of 1 to 10.

The identification of the production lot information can be achieved as follows.

For instance, light beams are emitted sequentially from three-component photodiodes of red, green and blue colors, or four-component photodiodes of white, red, green and blue colors to detect the hue marks of the production lot information identification portion.

For example, magnetoresistance sensor devices 800 for detecting magnetic fields, as shown in FIG. 3, are attached to a Printed Circuit Board (PCB) 704 having a small area in the measuring device or, as shown in FIG. 4, are attached to a biosensor connector so as to detect the magnetic field recorded on corresponding production lot information identification portions of the biosensor. Variations in resistance according to the intensity of the detected magnetic field are identified as digital information, which is transmitted to a calculation device. In turn, this calculation device compares the digital information with previously input production lot information, so that the production lot information of the biosensor can be identified.

In Step 3, measurement and operation processes of the biosensor measuring device are activated in conformity with the production lot information identified at Step 2.

Following the identification of the production lot information in Step 2, in greater detail, the measuring device has measurement and operation processes activated in conformity with the identified production lot information using a calibration curve, and enters a standby state for sample measurement.

Finally, Step 4 serves to introduce a liquid sample to the sample inlet of the biosensor to result in quantitative electrochemical information about the sample, quantify a specific component of the liquid sample, and display the quantified results.

In greater detail, the injection of a liquid sample into the biosensor strip inserted into the measuring device (step a) creates a predetermined potential difference between the working electrode and the auxiliary electrode and between the sample fluidity determining electrode and the auxiliary electrode (step b), and the sample flowing into the sample introducing portion of the strip causes primary electrical variation between the working electrode and the auxiliary electrode to adjust the voltages between the electrodes to the same value (step c). The sample fluidity determining electrode senses the flow of the sample to cause secondary electrical variation, and the voltage between the auxiliary electrode and the sample fluidity determining electrode is adjusted to be the same, thus providing information about the time difference with the electrical variation primarily sensed by the working electrode (step d). When a liquid sample is sufficiently mixed with a reagent applied to the working electrode, voltage is applied again between the working electrode and the auxiliary electrode to cause a cycling reaction in a parallel-type thin layer electrochemical cell, and the stationary current value thus reached is read (step e). The amount of the substrate present in the sample is analyzed using the time information obtained in step d and the stationary current value obtained in step e to determine the level of a specific component, such as blood glucose, and the result is displayed in a window.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An electrochemical biosensor, comprising:
  a plurality of electrodes including at least a working electrode and an auxiliary electrode prepared on at least one or two insulating plates;
  a sample introduction portion for introducing a sample into the electrodes;
  a reaction reagent layer, formed on the working electrode, containing a redox enzyme and an electron transfer mediator;
  an electrical connection portion for connecting the working electrode and the auxiliary electrode; and
  a production lot information identification portion configured such that production lot information is recorded on at least one insulating plate, which is selected from among at least two planar insulating plates and does not interrupt a connection between the electrodes,
  wherein the production lot information identification portion, configured such that the production lot information is recorded thereon, includes magnetization marks which display information about differences between production lots by means of differences in magnetic field intensity and are prepared by printing a magnetic material or attaching a magnetic film according to differences in magnetic field intensity in a predetermined pattern; and
  wherein the magnetization material or the magnetic film emits a magnetic field of 0.01~15 Gauss.

2. The electrochemical biosensor according to claim 1, wherein a number of the magnetization marks ranges from 1 to 10.

3. An electrochemical biosensor measuring device quantitatively determining analytes using the electrochemical biosensor set forth in claim 1, wherein the electrochemical biosensor measuring device comprises one or more magnetoresistance sensor devices of detecting magnetic fields to identify production lot information recorded on the production lot information identification portion of the biosensor.

4. The electrochemical biosensor measuring device according to claim 3, wherein the magnetoresistance sensor devices detect the magnetic field applied from the magnetization marks to discern production lot information according to difference in the intensity of the magnetic fields.

5. The electrochemical biosensor measuring device according to claim 3, wherein the magnetoresistance sensor devices are constructed in a separated structure such that a detection path of the magnetic field is provided outside the connector into which the biosensor is inserted for electrical connection.

6. The electrochemical biosensor measuring device according to claim 3, wherein the magnetoresistance sensor devices are constructed in an integrated structure such that a detection path of the magnetic field is provided at an upper or lower end portion of the connector, into which the biosensor is inserted for electrical connection.

7. A measuring method using the electrochemical biosensor measuring device according to claim 3, comprising:

inserting a biosensor provided with a production lot information identification portion into the connector port of the biosensor measuring device to activate its power (step 1);

identifying the production lot information of the inserted biosensor by allowing two or more magnetoresistance sensor devices to detect the information recorded on the production lot information identification portion provided in the biosensor (step 2);

activating the measurement and operation processes of the biosensor measuring device in conformity with the production lot information identified at Step 2 (step 3); and introducing a liquid sample into the sample inlet of the biosensor to result in quantitative electrochemical information about the sample, quantifying a specific component of the liquid sample, and displaying quantification results (step 4);

wherein the production lot information identification portion, configured such that the production lot information is recorded thereon, includes magnetization marks which display information about differences between production lots by means of differences in magnetic field intensity and are prepared by printing a magnetic material or attaching a magnetic film according to differences in magnetic field intensity in a predetermined pattern; and wherein the magnetization material or the magnetic film emits a magnetic field of 0.01~15 Gauss.

* * * * *